United States Patent
Schroeder

(10) Patent No.: US 10,945,979 B1
(45) Date of Patent: Mar. 16, 2021

(54) AMINO ACID COMPOSITIONS TO PROMOTE ENDOTHELIAL HEALTH

(71) Applicant: Carl Louis Schroeder, Shoreview, MN (US)

(72) Inventor: Carl Louis Schroeder, Shoreview, MN (US)

(73) Assignee: Carl Louis Schroeder, Shoreview, MN (US)

(*) Notice: Subject to any disclaimer, the term of this patent is extended or adjusted under 35 U.S.C. 154(b) by 30 days.

(21) Appl. No.: 15/841,003

(22) Filed: Dec. 13, 2017

Related U.S. Application Data

(60) Provisional application No. 62/433,561, filed on Dec. 13, 2016.

(51) Int. Cl.
| | |
|---|---|
| *A61K 31/198* | (2006.01) |
| *A61K 31/185* | (2006.01) |
| *A61K 9/48* | (2006.01) |
| *A61K 31/522* | (2006.01) |
| *A23L 33/175* | (2016.01) |
| *A23L 2/60* | (2006.01) |
| *C12G 3/04* | (2019.01) |
| *A61K 9/00* | (2006.01) |

(52) U.S. Cl.
CPC .............. *A61K 31/198* (2013.01); *A23L 2/60* (2013.01); *A23L 33/175* (2016.08); *A61K 9/0095* (2013.01); *A61K 9/48* (2013.01); *A61K 31/185* (2013.01); *A61K 31/522* (2013.01); *C12G 3/04* (2013.01); *A23V 2002/00* (2013.01)

(58) Field of Classification Search
CPC . A23L 33/175; A23L 2/38; A23L 2/39; A61K 31/198
See application file for complete search history.

(56) References Cited

U.S. PATENT DOCUMENTS

| | | | | |
|---|---|---|---|---|
| 2001/0033881 A1* | 10/2001 | Fuchs | ...................... | A23L 2/38 426/72 |
| 2004/0087515 A1* | 5/2004 | Butler | .................. | A61K 31/195 514/25 |
| 2008/0063689 A1* | 3/2008 | Farber | .................. | A61K 31/185 424/439 |
| 2014/0030241 A1* | 1/2014 | Greenberg | ........... | A61K 31/198 424/93.41 |

FOREIGN PATENT DOCUMENTS

| CN | 103263018 A | * | 8/2013 |
|---|---|---|---|
| CN | 105661234 A | * | 6/2016 |

OTHER PUBLICATIONS

Danica Benninghoven, What Foods Contain Taurine, Livestrong, [Retrieved from internet <URL: https://www.livestrong.com/article/157099-what-foods-contain-taurine/ >], (updated Jul. 22, 2019), 7 pages (Year: 2019).*
Rena Goldman, Healthline, 10 Healthy High-Arginine Foods, [Retrieved from internet <URL: https://www.healthline.com/health/healthy-high-arginine-foods >], (reviewed May 30, 2019), 14 pages (Year: 2019).*
Maura Wolf, Foods Containing L-Citrulline, LiveStrong.com, [Retrieved from internet <URL: https://www.livestrong.com/article/321823-foods-containing-citrulline/ >], [Downloaded Oct. 28, 2019], 14 pages (Year: 2019).*
NIH, NIAAA, What is a standard drink? Rethinking drinking—NIAAA, [Retrieved from internet <URL: https://www.rethinkingdrinking.niaaa.nih.gov/How-much-is-too-much/What-counts-as-a-drink/Whats-A-Standard-Drink.aspx >], [Downloaded Oct. 28, 2019], 1 page (Year: 2019).*
NIH, NIAAA, What is a standard drink?, [Retrieved from internet <URL: https://www.rethinkingdrinking.niaaa.nih.gov/How-much-is-too-much/What-counts-as-a-drink/Whats-A-Standard-Drink.aspx >], [Downloaded Oct. 28, 2019], 2 pages (Year: 2019 ).*
CN-103263018-A (Espacenet English translation, downloaded Nov. 2020) (Year: 2020).*
CN-105661234-A (Espacenet English translation, downloaded Nov. 2020) (Year: 2020).*
Bailey, S. et al., "Acute L-arginine supplementation reduces the O2 cost of moderate-intensity exercise and enhances high-intensity exercise tolerance," J Appl Physiol 109: 1394-1403, 2010.
Bailey, S. et al., "L-Citrulline supplementation improves O2 uptake kinetics and high-intensity exercise performance in humans," J Appl Physiol 119: 385-395, 2015.
Bloodsworth, A. et al., "Nitric Oxide Regulation of Free Radical- and Enzyme-Mediated Lipid and Lipoprotein Oxidation," Arterioscler Thromb Vasc Biol. 2000;20:1707-1715.
Bridges, C. et al., "Regulation of taurine transporter expression by NO in cultured human retinal pigment epithelial cells," Am J Physiol Cell Physiol, 281: C1825-C1836, 2001.
Chakroborty, S. et al., "Nitric Oxide Signaling Is Recruited As a Compensatory Mechanism for Sustaining Synaptic Plasticity in Alzheimer's Disease Mice," Journal of Neuroscience, Apr. 29, 2015, 35 (17) 6893-6902.
Cormio, L. et al., "Oral L-citrulline supplementation improves erection hardness in men with mild erectile dysfunction," Urology, Jan. 2011;77(1):119-22.

(Continued)

*Primary Examiner* — Mark V Stevens
(74) *Attorney, Agent, or Firm* — Merchant & Gould P.C.

(57) ABSTRACT

Amino acid compositions for promoting vascular endothelial health include arginine, citrulline, and taurine. Compositions may be combined with additional ingredients to form beverages, concentrates, and non-liquid food compositions. Methods of making concentrate compositions, beverage compositions, and non-liquid food compositions are provided. Methods of administering compositions to improve endothelial health, treat endothelial dysfunction, treat sexual dysfunction, treat altitude sickness, treat decompression sickness, treat jet lag, and treat fatigue include administering compositions including arginine, citrulline, and taurine.

24 Claims, 1 Drawing Sheet

(56) References Cited

OTHER PUBLICATIONS

Davignon, J. et al., "Role of Endothelial Dysfunction in Atherosclerosis," Circulation. 2004;109[suppl III]:III-27-III-32.).

Eby, G. et al., "Elimination of cardiac arrhythmias using oral taurine with I-arginine with case histories: Hypothesis for nitric oxide stabilization of the sinus node," Medical Hypotheses, 2006;67(5):1200-4. Epub Jun. 23, 2006.

Gaucher, D. et al., "Taurine deficiency damages retinal neurones: cone photoreceptors and retinal ganglion cells," Amino Acids (2012) 43:1979-1993.

Heffernan, K. et al., "L-Arginine as a Nutritional Prophylaxis Against Vascular Endothelial Dysfunction With Aging," J Cardiovasc Pharmacol Ther. Mar. 2010; 15(1): 17-23.

Ito, T. et al., "The potential usefulness of taurine on diabetes mellitus and its complications," Amino Acids, May 2012; 42(5): 1529-1539.

Lambert, I. et al., "Regulation of Taurine Transport Systems by Protein Kinase CK2 in Mammalian Cells," Cell Physiol Biochem 2011;28:1099-1110.

Martin, D. et al., "Design and conduct of 'Xtreme Alps': A double-blind, randomised controlled study of the effects of dietary nitrate supplementation on acclimatisation to high altitude," Contemporary Clinical Trials 36 (2013) 450-459.

Maxwell, A. et al., "L-Arginine enhances aerobic exercise capacity in association with augmented nitric oxide production," J. Appl Physiol 90: 933-938, 2001.

Metra, M. et al., "Vasodilators in the treatment of acute heart failure: what we know, what we don't," Heart Fail Rev (2009) 14:299-307.

Moncada, S. et al., "Nitric oxide, cell bioenergetics and neurodegeneration," Journal of Neurochemistry, 2006, 97, 1676-1689.

Morita, M. et al., "Oral supplementation with a combination of L-citrulline and L-arginine rapidly increases plasma L-arginine concentration and enhances NO bioavailability," Biochemical and Biophysical Research Communications 454 (2014) 53-57.

Muhm, J. et al., "Effect of Aircraft-Cabin Altitude on Passenger Discomfort," N Engl J Med 2007;357:18-27.

Musicki, B. et al., "Endothelial Nitric Oxide Synthase Regulation in Female Genital Tract Structures," J Sex Med. Mar. 1, 2009; 6(S3PROCEEDINGS): 247-253.

Nakaya, Y. et al., "Taurine improves insulin sensitivity in the Otsuka Long-Evans Tokushima Fatty rat, a model of spontaneous type 2 diabetes," Am J Clin Nutr, 2000;71:54-8.

Paul, V. et al., "Involvement of nitric oxide in learning & memory processes," Indian J Med Res. May 2011; 133(5): 471-478.

Ripps, H. et al., "Review: Taurine: A "very essential" amino acid," Mol Vis. 2012; 18: 2673-2686.

Schlaich, M. et al., "Impaired L-Arginine Transport and Endothelial Function in Hypertensive and Genetically Predisposed Normotensive Subjects," Circulation. 2004;110:3680-3686.

Schneider, J-C. et al., "Response of nitric oxide pathway to L-arginine infusion at the altitude of 4,350 m," Eur Respir J 2001; 18: 286-292.

Sun, Q. et al., "Taurine Supplementation Lowers Blood Pressure and Improves Vascular Function in Prehypertension Randomized, Double-Blind, Placebo-Controlled Study," Hypertension. 2016; 67:541-549.

Totzeck, M. et al., "Nitrite Regulates Hypoxic Vasodilation via Myoglobin-Dependent Nitric Oxide Generation," Circulation. 2012;126:325-334.

Xu, Y-J. et al., "The potential health benefits of taurine in cardiovascular disease," Exp Clin Cardiol. 2008; 13(2):57-65.

Zhang, Y. et al., "Modulating endothelial nitric oxide synthase: a new cardiovascular therapeutic strategy," Am J Physiol Heart Circ Physiol 301: H634-H646, 2011.

Zulli, A. et al., "High Dietary Taurine Reduces Apoptosis and Atherosclerosis in the Left Main Coronary Artery Association With Reduced CCAAT/Enhancer Binding Protein Homologous Protein and Total Plasma Homocysteine but not Lipidemia," Hypertension, 2009; 53:1017-1022.

"L-Arginine," Bio-Chemicals Business Unit, Dec. 2005, pp. 1-25.

De la Puerta, et al., "Taurine and Glucose Metabolism: a review," Nutrición Hospitalaria, Feb. 25, 2010, vol. 25, No. 6, Madird, Nov./Dec. 201, 13 pages.

Aung, H. et al., "Alternative Therapies for Male and Female Sexual Dysfunction," The American Journal of Chinese Medicine, vol. 32, No. 2, pp. 161-173 (2004).

Bailey, S. et al., "Acute L-arginine supplementation reduces the O2 cost of moderate-intensity exercise and enhances high-intensity exercise tolerance," J Appl Physiol 109: pp. 1394-1403, 2010.

Bailey, S. et al., "L-Citrulline supplementation improves O2 uptake kinetics and high-intensity exercise performance in humans," J Appl Physiol 119: pp. 385-395, 2015.

Bloodsworth, A. et al., "Nitric Oxide Regulation of Free Radical- and Enzyme-Mediated Lipid and Lipoprotein Oxidation," Arterioscler Thromb Vasc Biol. Jul. 2000; pp. 1707-1715.

Bridges, C. et al., "Regulation of taurine transporter expression by NO in cultured human retinal pigment epithelial cells," Am J Physiol Cell Physiol, 281: pp. C1825-C1836, 2001.

Chakroborty, S. et al., "Nitric Oxide Signaling Is Recruited As a Compensatory Mechanism for Sustaining Synaptic Plasticity in Alzheimer's Disease Mice," Journal of Neuroscience, Apr. 29, 2015, 35 (17), pp. 6893-6902.

Chesney, R. et al., "Taurine and the renal system," Journal of Biomedical Science, 2010, 17(Suppl 1):S4, 10 pages.

Cooke, J., "The Cardiovascular Cure" How to Strengthen Your Self-Defense Against Heart Attack and Stroke (Excerpts from book), (1983), 2 pages.

Cormio, L. et al., "Oral L-citrulline supplementation improves erection hardness in men with mild erectile dysfunction," Urology, Jan. 2011;77(1):119-22; 2 pages.

Davignon, J. et al., "Role of Endothelial Dysfunction in Atherosclerosis," Circulation. 2004;109[suppl III]:III-27-III-32.); 7 pages.

De Luca, A. et al., "Taurine: the appeal of a safe amino acid for skeletal muscle disorders," J.Transl Med (2015) 13:243; 18 pages.

Eby, G. et al., "Elimination of cardiac arrhythmias using oral taurine with I-arginine with case histories: Hypothesis for nitric oxide stabilization of the sinus node," Medical Hypotheses, 2006;67(5):1200-4. Epub Jun. 23, 2006, 5 pages.

Furchgott, R. et al., "Physiology or Medicine for 1998—Animation". Nobelprize.org. Nobel Media AB 2014 Web. Jun. 6, 2015.

Gaucher, D. et al., "Taurine deficiency damages retinal neurones: cone photoreceptors and retinal ganglion cells," Amino Acids (2012) 43:1979-1993, 15 pages.

Ghandforoush-Sattari, M. et al., "Pharmacokinetics of Oral Taurine in Healthy Volunteers," Journal of Amino Acids. vol. 2010, Article ID 346237, 5 pages.

Greene, W., "Nitric Oxide (NO)," DC Nutrition, 5 pages (Copyright 1999-2017).

Hayashi, T. et al., "L-citrulline and L-arginine supplementation retards the progression of high-cholesterol-diet-induced atherosclerosis in rabbits," PNAS, vol. 102, No. 38, pp. 13681-13686 (Sep. 20, 2005).

Heffernan, K. et al., "L-Arginine as a Nutritional Prophylaxis Against Vascular Endothelial Dysfunction With Aging," J Cardiovasc Pharmacol Ther. Mar. 2010; 15(1): pp. 17-23.

Hefti, J. et al., "Oxidative Stress in Hypobaric Hypoxia and Influence on Vessel-Tone Modifying Mediators," High Altitude Medicine & Biology, vol. 14, No. 3, pp. 273-279 (2013).

Ito, T. et al., "Taurine depletion caused by knocking out the taurine transporter gene leads to cardiomyopathy with cardiac atrophy," Journal of Molecular and Cellular Cardiology, vol. 44, No. 5, pp. 927-937 (May 2008).

Ito, T. et al., "The potential usefulness of taurine on diabetes mellitus and its complications," Amino Acids, May 2012; 42(5): 1529-1539, 15 pages.

Lambert, I. et al., "Regulation of Taurine Transport Systems by Protein Kinase CK2 in Mammalian Cells," Cell Physiol Biochem 2011;28: pp. 1099-1110.

L-Citrulline Proven to Restore Erectile Function Via Nitric Oxide, Not Just Temporary Like Viagra, Qivana, 7 pages (2013).

(56) References Cited

OTHER PUBLICATIONS

Macleavy, I. "The Forgotten Longevity Benefits of Taurine," Life Extension Magazine, 15 pages (Jun. 2013).
Mangoni, A. et al., "Transsulfuration Pathway Thiols and Methylated Arginines: The Hunter Community Study," PLOS ONE, vol. 8, Issue 1, e54870, pp. 1-8 (Jan. 2013).
Martin, D. et al., "Design and conduct of 'Xtreme Alps': A double-blind, randomised controlled study of the effects of dietary nitrate supplementation on acclimatisation to high altitude," Contemporary Clinical Trials 36 (2013) pp. 450-459.
Maxwell, A. et al., "L-Arginine enhances aerobic exercise capacity in association with augmented nitric oxide production," J. Appl Physiol 90: pp. 933-938, 2001.
Metra, M. et al., "Vasodilators in the treatment of acute heart failure: what we know, what we don't," Heart Fail Rev (2009) 14: pp. 299-307.
Moncada, S. et al., "Nitric oxide, cell bioenergetics and neurodegeneration," Journal of Neurochemistry, 2006,97, pp. 1676-1689.
Morita, M. et al., "Oral supplementation with a combination of L-citrulline and L-arginine rapidly increases plasma L-arginine concentration and enhances NO bioavailability," Biochemical and Biophysical Research Communications 454 (2014) pp. 53-57.
Muhm, J. et al., "Effect of Aircraft-Cabin Altitude on Passenger Discomfort," N Engl J Med 2007;357: pp. 18-27.
Musicki, B. et al., "Endothelial Nitric Oxide Synthase Regulation in Female Genital Tract Structures," J Sex Med. Mar. 1, 2009; 6(S3PROCEEDINGS): 247-253, 10 pages.
Nakaya, Y. et al., "Taurine improves insulin sensitivity in the Otsuka Long-Evans Tokushima Fatty rat, a model of spontaneous type 2 diabetes," Am J Clin Nutr, 2000;71: pp. 54-58.
Paul, V. et al., "Involvement of nitric oxide in learning & memory processes," Indian J Med Res. May 2011; 133(5): 471-478, 11 pages.
Ripps, H. et al., "Review: Taurine: A "very essential" amino acid," Mol Vis. 2012; 18: 2673-2686, 20 pages.
Rosick, E., "Arginine Fights Coronary Artery Disease," Life Enhancement, 5 pages (Aug. 2002).
Schlaich, M. et al., "Impaired L-Arginine Transport and Endothelial Function in Hypertensive and Genetically Predisposed Normotensive Subjects," Circulation. 2004;110: 3680-3686, 8 pages.
Schneider, J-C. et al., "Response of nitric oxide pathway to L-arginine infusion at the altitude of 4,350 m," Eur Respir J 2001; 18: 286-292, 7 pages.
Stephan, B. et al., "Cardiovascular Disease, the Nitric Oxide Pathway and Risk of Cognitive Impairment and Dementia," Current Cardiology Reports, 19(9):87 Sep. 2017, 10 pages.
Sun, Q. et al., "Taurine Supplementation Lowers Blood Pressure and Improves Vascular Function in Prehypertension Randomized, Double-Blind, Placebo-Controlled Study," Hypertension. 2016; 67: 541-549, 24 pages.
Totzeck, M. et al., "Nitrite Regulates Hypoxic Vasodilation via Myoglobin-Dependent Nitric Oxide Generation," Circulation. 2012;126: 325-334, 29 pages.
Witting, P. et al., "Reaction of Human Myoglobin and Nitric Oxide," The Journal of Biological Chemistry, vol. 276, No. 6, pp. 3991-3998 (Feb. 9, 2001).
Wojcik, O. et al., "The potential protective effects of taurine on coronary heart disease," Atherosclerosis. Jan. 2010; 208 (1): 19, 11 pages.
Xu, Y-J. et al., "The potential health benefits of taurine in cardiovascular disease," Exp Clin Cardiol. 2008; 13(2): 57-65, 9 pages.
Yoshitomi, H. et al., "L-Citrulline increases hepatic sensitivity to insulin by reducing the phosphorylation of serine 1101 in insulin receptor substrate-1," BMC Complementary and Alternative Medicine, (2015) 15: 188, 11 pages.
Zhang, Y. et al., "Modulating endothelial nitric oxide synthase: a new cardiovascular therapeutic strategy," Am J Physiol Heart Circ Physiol 301: H634-H646, 2011, 13 pages.
Zulli, A. et al., "High Dietary Taurine Reduces Apoptosis and Atherosclerosis in the Left Main Coronary Artery Association With Reduced CCAAT/Enhancer Binding Protein Homologous Protein and Total Plasma Homocysteine but not Lipidemia," Hypertension, 2009; 53: 1017-1022, 18 pages.
Thomas Burke Ph.D., "Nitric Oxide and its Role in Health and Diabetes," Diabetes in Control News and Information for Medical Professionals, http://www.diabetesincontrol.com/burkearchive/, Aug. 7, 2009, pp. 1-24.
Mark S. Segal Ph.D., "Nitric Oxide Holds Promise for Diabetes Cell Repair," Journal of Diabetes, 2 pages, Jan. 2006.
Wollman et al., "Effect of Oral Administration of High-Dose Nitric Oxide Donor L-Arginine in Men with Organic Erectile Dysfunction: Results of a Double-Blind, Randomized, Placebo-Controlled Study," BJU International (1999), vol. 83., pp. 269-273.
Meldrum, et al., "Erectile Hydraulics: Maximizing Inflow while Minimizing Outflow," International Society for Sexual Medicine (2014), vol. 11, pp. 1208-1220.
Arthur L. Burnett, MD, "The Role of Nitric Oxide in Erectile Dysfunction: Implications for Medical Therapy," The Journal of Clinical Hypertension, Dec. 2006, vol. 8, No. 12, pp. 53-62.
Miyazaki et al., "Taurine and Liver Diseases: A Focus on the Heterogeneous Protective Properties of Taurine," Amino Acids (2014), vol. 46, pp. 101-110.
Froger, et al., "Taurine: The Comeback of a Neutraceutical in the Prevention of Retinal Degenerations," Progress in Retinal and Eye Research (2014), vol. 41, pp. 44-63.
Santa-Maria, et al., "Taurine, an Inducer for Tau Polymerization and a Weak Inhibitor for Amyloid-β-Peptide Aggregation," ScienceDirect (2007), vol. 429, pp. 91-94.
"L-Arginine," Bio-Chemicals Business Unit, Dec. 2005, pp. 1-27.
Chen, et al., "Arginine and Antioxidant Supplement on Performance in Elderly Male Cyclists: A Randomized Controlled Trial," BioMedCentral, (2010), vol. 7, No. 13, pp. 1-10.
Rahman, et al., "Taurine Prevents Hypertension and Increases Exercise Capacity in Rats with Fructose-Induced Hypertension," American Journal of Hypertension, vol. 24, Issue 5, May 2011, pp. 574-581.
Schwedhel, et al. "Pharmacokinetic and Pharmacodynamic Properties of Oral L-Citrulline and L-Arginine: Impact on Nitric Oxide Metabolism," British Journal of Clinical Pharmacology, Jan. 2008, vol. 65, No. 1, pp. 51-59.
VanHoutte, "Nitric Oxide-Protector of the Endothelium (Lining of the Arteries)," Mayo Clinic (1983), 6 pages.
Abebe, et al., "Role of Taurine in the Vasculature: An Overview of Experimental and Human Studies," AM J. Cardiovasc Dis. (2011), vol. 1, No. 3, pp. 293-311.
Karabacak, et al., "Effects of Taurine on Contractions of Human Internal Mammary Artery: A Potassium Channel Opening Action," European Review for Medical and Pharmacological Sciences (2015), vol. 19, pp. 1498-1504.
Kyowa Hakko Kogyo Co., Ltd, "L-Citrulline," http://www.kyowa.co.jp/, (2005), 25 pages.
Balez, et al., "Getting to NO Alzheimer's Disease: Neuroprotection Versus Neurotoxicity Mediated by Nitric Oxide," Illawarra Health and Medical Research Institute, School of Biological Sciences, University of Wollongong, Wollongong, NSW 2522, Australia, Jul. 3, 2015, 9 pages.
Lin et al., "Impaired Nitric Oxide Synthase Pathway in Diabetes Mellitus," http://ahajournals.org, Sep. 2, 2018, pp. 987-992.
"L-Citrulline Supplements Enhance Arterial Stiffness in Postmenopausal Women," Qivana, Apr. 2013, pp. 1-2.
Askwith, et al., "Taurine Reduces Nitrosative Stress and Nitric Oxide Synthase Expression in High Glucose-Exposed Human Schwann Cells," Exp. Neurol., Jan. 2012, vol. 233, No. 1, pp. 154-162.
Ortiz, et al., "Renal Response to L-Arginine in diabetic Rats. A Possible Link Between Nitric Oxide System and Aquaporin-2," PLOS One, httP://dx.doi.org/10.1371/journal.pone.0104923, Aug. 11, 2014, 12 pages.
Beall, et al., "Nitric Oxide in Adaptation to Altitude," Free Radic biol Med., Apr. 1, 2012, vol. 52, No. 7, pp. 1123-1134.
"Altitude Sickness," https://humanresearchwiki.jsc.nasa.gov/index.php?title=Altitude_Sickness, Jun. 14, 2016, pp. 1-6.
Maia, et al., "Taurine Supplementation Reduces Blood Pressure and Prevents Endothelial Dysfunction and Oxidative Stress in Post-

(56) References Cited

OTHER PUBLICATIONS

Weaning Protein-Restricted Rats," PLOS One, www.plosone.org, Aug. 2014, vol. 9, Issue 8, pp. 1-10.
De la Puerta, et al., "Taurine and Glucose Metabolism: a review," Nutrición Hospitalaria, Feb. 25, 2010, vol. 25, No. 6, Madird, Nov./Dec. 2010, 13 pages.
Erzurum, et al., "Higher blood flow and circulating NO products offset high-altitude hypoxia among Tibbetans," Proceedings of the National Academy of Sciences of the United States of America, Nov. 6, 2007, Vole 104, No. 45, pp. 17593-17598.

* cited by examiner

AMINO ACID COMPOSITIONS TO PROMOTE ENDOTHELIAL HEALTH

CROSS-REFERENCE TO RELATED APPLICATION

This application claims the benefit of U.S. Provisional Application No. 62/433,561, filed Dec. 13, 2016, which is hereby incorporated by reference in its entirety.

FIELD

The present disclosure relates to amino acid compositions for promoting vascular endothelial health by enhancing nitric oxide (NO) production. In particular, the present disclosure relates to nutritional compositions having arginine, citrulline, and taurine and methods of using the same.

BACKGROUND

Nutritional Supplements

Nutritional supplements are commonly used to remedy health deficiencies, boost energy, and improve bodily functions. Various products have been developed to deliver health boosting ingredients including beverages, pills, chews, and nutrition bars. Such products may include nutritional supplements such as protein, fiber, or vitamins. Some products provide enough nutrition to replace meals. Products may be designed with a particular combination of nutrients and ingredients to correct a particular deficiency or boost the functioning of a particular process in the body. For example, a product may be designed to promote muscle healing or growth to maximize the effects of weight training. Other products may focus on improving mental function.

A subset of products are aimed at boosting energy. Energy drinks typically include a combination of simple carbohydrates, vitamins, and caffeine. Various combinations of ingredients may be used to increase energy and alertness in an individual. These products may come in the form of chews, drinks, or "shots"—small quantities of beverage intended to be ingested quickly. Some energy drinks may include alcohol or may be mixed with alcohol to produce a cocktail or other alcoholic beverage. Such products are popular for recreational use in social settings. Energy drinks may involve one or more active ingredients in addition to caffeine and/or sugar or may rely entirely upon the active ingredients to provide an energy boost.

Nitric Oxide and Vasodilation

Nitric Oxide (NO) is an important signaling molecule involved in endothelial health. NO is synthesized in vascular endothelial cells by an isoform of nitric oxide synthase (NOS) from arginine and molecular oxygen. Nitric oxide has been shown to improve vasodilation. The endothelium (inner lining) of blood vessels uses NO to signal to surrounding muscles to relax, resulting in increased blood flow. Increased vasodilation has been linked to preventing endothelial malfunction. Dysfunction of the endothelial NO pathway contributes to the pathophysiology of a variety of diseases such as hypertension, type I and II diabetes, hypercholesterolanemia, and sexual dysfunction.

The endothelial NO pathway is of particular interest for treating sexual dysfunction in women, as existing pharmaceutical treatments focus on inhibiting PDE-5, which increases cGMP availability, thereby increasing blood delivery to the genitals. However, women have very little PDE-5 compared to men, so PDE-5 inhibitors are not always effective.

NO is produced in endothelial cells and diffuses across vascular smooth muscle cell membranes to activate the enzyme soluble guanylate cyclase (sGC). sGC catalyzes the conversion of guanosine triphosphate into cyclic guanosine monophosphate (cGMP), which then activates protein kinase G (PKG). PKG phosphorylates various targets that trigger a reduction in calcium ions which results in vascular relaxation.

It is against this background that the present disclosure is made.

SUMMARY

In general terms, this disclosure is directed to improving endothelial health by administering a composition including arginine, citrulline, and taurine.

In one aspect, a composition for promoting vascular endothelial health is provided that includes arginine, citrulline, and taurine.

In another aspect, a concentrated liquid composition is provided for promoting vascular endothelial health that includes arginine, citrulline, taurine, sweetener, functional ingredients, and water. The composition may be in the form of an alcoholic beverage composition that increases vasodilation and includes arginine, citrulline, taurine, and alcoholic beverage. In another aspect, an enhancer water beverage composition is provided that includes arginine, citrulline, taurine, sweetener, water, and functional ingredients. The composition may be a solid composition for promoting vascular endothelial health and includes arginine, citrulline, taurine, protein source, carbohydrate source, and additional ingredients. In yet another aspect, a gel composition for increasing vasodilation is provided that includes arginine, citrulline, taurine, gelling agent, carbohydrate, and additional ingredients.

The present disclosure is also directed to methods of treating endothelial dysfunction, sexual dysfunction, jet lag, altitude sickness, decompression sickness, and fatigue by administering to an individual a composition that includes arginine, citrulline, and taurine. In another aspect, a method of improving endothelial health in a human or an animal is provided by administering a composition including arginine, citrulline, and taurine.

DETAILED DESCRIPTION

Figure 1A:
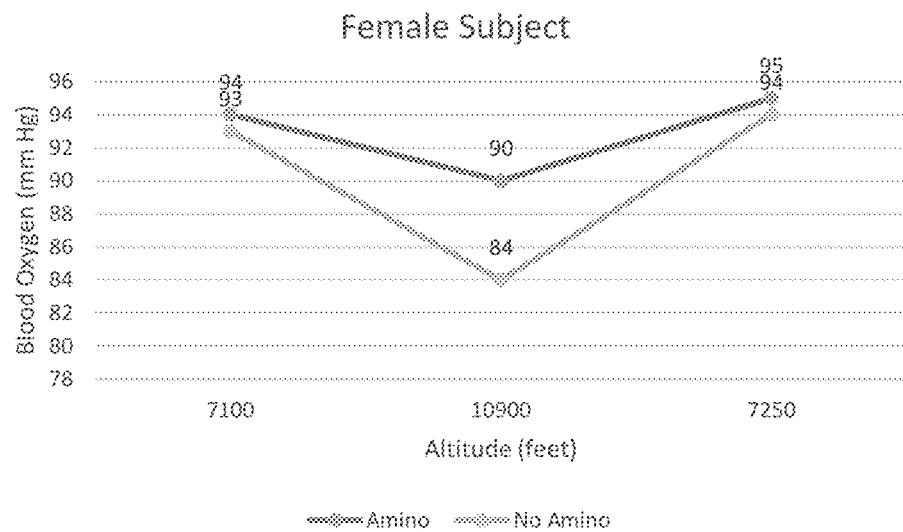
FIG. 1A depicts a graph comparing blood oxygen levels for a female subject having consumed or not consumed the claimed composition at various altitudes.

The present disclosure is related to nutritional compositions having a combination of amino acids to enhance vasodilation and vascular health. In particular, the compositions include arginine, citrulline, and taurine to increase nitric oxide (NO) production, thereby improving endothelial vascular health in an individual. Methods of administering the composition and making the composition are also provided.

The nutritional compositions of the present disclosure include arginine in combination with a plurality of amino acids and other compounds to increase vasodilation for the improvement of vascular endothelial cell health. In particular, various combinations of arginine, citrulline, and taurine deliver superior benefits by providing improved concentrations of NO in vascular endothelial cells. Without wishing to be bound by theory, it is hypothesized that the nutritional compositions described in this disclosure aid in vasodilation by increasing the bioavailability of NO through modulation of the nitric oxide synthase (NOS) enzyme in endothelial cells. The nutritional compositions of the present disclosure may be administered to humans and other animals.

The synergistic effect from consuming arginine, citrulline and taurine starts with consuming enough of the amino acids to allow digestion and entry into the blood system. Once in the blood system, citrulline blocks the enzyme arginase allowing additional arginine to enter the blood stream via the liver and kidneys and travels to the endothelium for conversion into NO. Citrulline will remain available in the blood stream for many hours and act as an arginine bank available to be converted into arginine when needed. Taurine travels via the blood system to various organs and cells. In smooth muscle cells taurine enhances cellular health and the ability of smooth muscle to absorb NO, resulting in vasodilation.

An individual could benefit from the effects of NO-dependent responses in as little as 1 hour after ingesting the nutritional composition. In some embodiments an individual may ingest the nutritional composition for an immediate effect, but not on a regular basis. For instance, one may ingest the composition before physical activity to benefit from a boost in NO production. Alternatively, in other embodiments, an individual may take regular doses of the composition to maintain improved NO production over a longer period of time in order to improve endothelial health.

The following amino acids may be provided in the form of salts. Such salts may include acid addition salts, metal salts, ammonium salts, organic amine addition salts, amino acid addition salts and the like.

Arginine

Arginine described in the present disclosure includes L-arginine or D-arginine, and is preferably L-arginine. Arginine, or salts thereof, described in the present disclosure may be obtained by using various methods including chemical synthesis and may also be a commercially available product. Arginine is a precursor in the synthesis of nitric oxide (NO). Nitric oxide synthase (NOS) converts L-arginine, NADPH, and oxygen into citrulline, NO, water, and NADP. When arginine is converted into NO, the NO signals to smooth muscle to relax, thereby promoting vasodilation and increased blood flow.

Arginine provides additional health benefits including reducing healing time and decreasing blood pressure. To be most effective, arginine is preferably administered to a human in an amount of about 4 to 15 grams per day. Dosages for humans will vary depending on the size of the individual. Preferably, compositions of the present disclosure should provide an individual with an amount of arginine ranging from about 2 g to about 12 g per day, preferably from about 3 g to about 10 g per day. Preferably, an individual will ingest about 3-10 grams of arginine per serving (e.g., per serving of a pill, beverage, or food product). The arginine is preferably present in a concentration of about 0.1 wt-% to about 60 wt-% depending on the form of the composition.

Citrulline

Nutritional compositions of the present disclosure include citrulline. Citrulline is a non-protein amino acid that is found in significant dietary amounts only in watermelon (*Citrullus lanatus*). Citrulline described in the present disclosure includes L-citrulline, D-citrulline, or citrulline malate. L-citrulline is preferably included. Citrulline, or salts thereof, may be obtained by using various methods including chemical synthesis and may also be a commercially available product.

Citrulline plays several roles in nitric oxide production and levels of NO. In the liver citrulline is converted into arginine and enters the blood stream. Citrulline also inhibits an enzyme in the liver that breaks down approximately 40% of ingested arginine, thus providing more arginine for NO production. Citrulline acts as a "bank" for conversion into arginine. In the conversion of arginine into NO some citrulline is formed as a byproduct and the citrulline circulates in the blood stream until arginine levels drop and then the body calls for citrulline and this leads to the arginine reaction and then NO production. Studies have found that L-citrulline supplementation dose-dependently increases plasma L-arginine levels in healthy humans more effectively than effective doses of L-arginine itself.

To be most effective, citrulline is preferably administered to a human in an amount of 150 mg to about 12 g grams daily. Preferably, an individual will ingest about 50 mg to about 10 g per day, more preferably from about 1 g to about 9 g of cirtulline per day. Preferably, an individual will ingest about 3 grams of arginine per serving of a pill, beverage, or food product. The citrulline is preferably present in a concentration of about 0.05 wt-% to about 50 wt-% depending on the form of the composition.

Taurine

Nutritional compositions of the present disclosure include taurine. Taurine is a sulfur containing amino acid that has also been shown to modulate calcium channels in smooth muscle tissue. The modulation of smooth muscle calcium channels has been shown to enhance vascular endothelial cell health. Taurine described in the present disclosure includes L-taurine or D-taurine, and is preferably L-taurine. Taurine, or salts thereof, may be obtained by using various methods including chemical synthesis and may also be a commercially available product. Taurine's primary role is cell health. Taurine is a known osmolyte, ion channel regulator, intracellular calcium regulator, and anti-oxidant. In the vascular system, taurine plays a role in vasorelaxation, decreasing blood pressure, and decreasing atherosclerotic plaque. Taurine is commonly used in supplements for athletes due to its anti-fatigue and energizing properties.

Taurine contributes to vasodilation in more than one way. First, taurine acts as an antioxidant and increases eNOS expression, which in turn produces more NO. Taurine also reduces calcium ion concentrations in smooth muscle cells which relaxes the smooth muscle. This is important because calcium and potassium pumps play a crucial role in allowing NO to enter smooth muscle cells.

To be most effective, taurine is preferably administered to a human in an amount of 0.1-20 grams per day. Preferably, an individual will ingest from about 0.5 g to about 10 g per day, more preferably from about 1 g to about 6 g per day. Preferably, an individual will ingest about 2 grams of taurine per serving of a pill, beverage, or food product. The taurine is preferably present in a concentration of about 0.01 wt-% to about 40 wt-% depending on the form of the composition.

Sweeteners

In some embodiments, sweeteners may be added to the composition to mask the taste of the amino acids and improve the overall flavor of the compositions. Such sweeteners may include caloric, low-caloric, or non-caloric sweeteners that are artificial or natural. Some sugars interact with amino acids resulting in a browning reaction and are preferably avoided.

Natural caloric sweeteners include granulated sugars such as sucrose (white granulated sugar), glucose/dextrose, fructose, and galactose. These sugars may be derived from sugar cane or sugar beet and are dehydrated to form crystals. Sugar may be derived from other natural sources such as coconut palm sugar, date sugar, and palm sugar. Various natural syrups may also serve as sweeteners including maple syrup, agave nectar, molasses, honey, brown rice syrup, yacon syrup, sweet sorghum syrup, sugar beet syrup, barley malt syrup, and cane juice. Fruit juice concentrates may also serve as a natural source of sweetness in the compositions. Monosaccharides such as ribose may also be included. Ribose may include L-ribose and D-ribose.

The sweetener may be an artificial, non-caloric sweetener. The most common artificial sweeteners that are generally recognized as safe (GRAS) include saccharin, sucralose, aspartame, and acesulfame potassium. These sweeteners taste much sweeter than sugar and may be used in smaller quantities in the compositions.

Many natural non-caloric or low-caloric sweeteners are available and may be used in the compositions. *Stevia* is one of several non-caloric high-intensity natural sweeteners from the plant *Stevia rebaudiana* bertoni which produces a number of sweet compounds collectively referred to as steviol glycosides, making *stevia* 300 times sweeter than sucrose alone. Mogroside is another natural sweetener derived from monk fruit. Mogroside is sweeter than sugar and has fewer calories. Various natural sugar alcohols may also be used in the composition. These include erythritol, xylitol, sorbitol, maltitol, and mannitol. Sugar alcohols are less sweet and have fewer calories than sugar. Sugar alcohols may also provide thickening effects to compositions. In particular, sugar alcohols are beneficial in that they are less prone to browning than some other sweeteners.

In embodiments, the sweetener may be present in the composition in an amount from about 1% to about 75% by weight of the composition, depending on the form of the composition and the type of sweetener used. In some embodiments, caloric sweeteners are completely excluded.

Water

In some exemplary compositions, water is added in addition to the water that may be present with other materials (e.g., sweetener, functional ingredients, etc.). The amount of water utilized in the present nutritional compositions depends on the form of the composition. Water may also be used to dilute exemplary concentrate compositions. The water may be carbonated in some embodiments.

The present composition may be in the form of a beverage that is ready to drink. Typically, ready-to-drink beverage compositions comprise about 40 wt-% to about 99 wt-% water, preferably about 50 wt-% to about 95 wt-% water, and most preferably from about 55 wt-% to about 90 wt-% water.

The present composition may also be in the form of a liquid concentrate. These concentrates according to the present invention may be provided as, for example, a syrup and/or an aqueous concentrate. The liquid concentrate is typically formulated to provide a drinkable beverage composition wherein the concentrate is reconstituted or diluted with water or other aqueous fluid or liquid. Alternatively, liquid concentrate compositions may be ingested quickly as a "shot." Exemplary liquid concentrates typically comprise from about 5 wt-% to about 50 wt-% water, preferably from about 10 wt-% to about 40 wt-% water, and most preferably from about 15 wt-% to about 30 wt-% water.

Solid forms of the present composition contain little or no water. These compositions may include non-liquid food compositions and dry concentrates. Typically, exemplary solid forms of the present composition comprise from about 0 wt-% to about 20 wt-% water, preferably from about 0.5 wt-% to about 10 wt-% water, and most preferably from about 1 wt-% to about 5 wt-% water.

Functional Ingredients

Compositions of the present invention may optionally include one or more functional ingredients. Such functional ingredients may include flavoring agents, flavor enhancers, flavanols, acidulants/food acids, coloring agents, preservatives, antioxidants, alertness aids, alcohol, herbs, spices, extracts, vitamins, minerals, amino acids, fatty acids, juices, solid foods, and other edible ingredients.

Such optional functional ingredients may be dispersed, solubilized, or otherwise mixed into the present compositions. These components may be added to the compositions herein provided they do not substantially hinder the properties of the composition—namely, increasing endothelial health and vasodilation.

Flavanols

Flavanols are natural substances present in a variety of plants (e.g., fruits, vegetables, and flowers). The flavanols which may be utilized in the present invention can be extracted from, for example, fruit, vegetables, or other natural sources by any suitable method well known to those skilled in the art. For example, flavanols may be extracted from either a single plant or mixtures of plants. Many fruits, vegetables, flowers and other plants containing flavanols are known to those skilled in the art. Alternatively, these flavanols may be prepared by synthetic or other appropriate chemical methods and incorporated into the present compositions. Flavanols, including catechin, epicatechin, and their derivatives are commercially available.

Acidulants/Food Acids

The present compositions may optionally comprise one or more acidulants. An amount of an acidulant may be used to maintain the pH of the composition. Beverage acidity can be adjusted to and maintained within the requisite range by known and conventional methods, e.g., the use of one or more acidulants. Typically, acidity within the above recited ranges is a balance between maximum acidity for microbial inhibition and optimum acidity for the desired beverage flavor.

Organic as well as inorganic edible food acids may be used to adjust the pH of the beverage. The acids can be present in their undissociated form or, alternatively, as their respective salts, for example, potassium or sodium hydrogen phosphate, potassium or sodium dihydrogen phosphate salts. The preferred acids are edible organic acids which include citric acid, phosphoric acid, malic acid, fumaric acid, adipic acid, gluconic acid, tartaric acid, ascorbic acid, acetic acid, phosphoric acid or mixtures thereof. The most preferred acids are citric and phosphoric acids.

Coloring Agents

Small amounts of one or more coloring agents may be utilized in the compositions of the present invention. Beta-carotene or zeaxanthin may be used. Riboflavin and FD&C dyes (e.g., yellow #5, blue #2, red #40) and/or FD&C lakes may also be used. By adding the lakes to the other powdered ingredients, all the particles, in particular the colored iron compound, are completely and uniformly colored and a uniformly colored beverage mix is attained. Additionally, a mixture of FD&C dyes or a FD&C lake dye in combination with other conventional food and food colorants may be used. Additionally, other natural coloring agents may be utilized including, for example, chlorophylls and chlorophyllins, as well as fruit, vegetable, and/or plant extracts such as grape, black currant, aronia, carrot, beetroot, red cabbage, and hibiscus. Natural colorants are preferred for "all natural" food and drink compositions.

Flavoring Agents

One or more flavoring agents are recommended for the present invention in order to enhance their palatability. Any natural or synthetic flavor agent can be used in the present invention. For example, one or more botanical and/or fruit flavors may be utilized herein. As used herein, such flavors may be synthetic or natural flavors.

Particularly preferred fruit flavors are exotic and lactonic flavors such as, for example, passion fruit flavors, mango flavors, pineapple flavors, cupuacu flavors, guava flavors, cocoa flavors, papaya flavors, peach flavors, and apricot flavors. Besides these flavors, a variety of other fruit flavors can be utilized such as, for example, apple flavors, citrus flavors, grape flavors, raspberry flavors, cranberry flavors, cherry flavors, and the like. These fruit flavors can be derived from natural sources such as fruit juices and flavor oils, or may alternatively be synthetically prepared. The natural flavorants are preferred for "all natural" food and drink compositions.

Preferred botanical flavors include, for example, aloe vera, guarana, ginseng, ginkgo, hawthorn, hibiscus, rose hips, chamomile, peppermint, fennel, ginger, licorice, lotus seed, schizandra, saw palmetto, sarsaparilla, safflower, St. John's Wort, curcuma, cardimom, nutmeg, cassia bark, buchu, cinnamon, jasmine, haw, chrysanthemum, water chestnut, sugar cane, lychee, bamboo shoots, vanilla, coffee, and the like. Besides serving as sources of alertness, tea extracts and coffee can also be used as a flavoring agent.

In embodiments, flavoring agents may be added to the compositions of the present disclosure to mask any unpleasant tastes of certain supplements and active ingredients included in the composition. Flavorants may include those flavors within the purview of those skilled in the art, such as natural and artificial flavors. These flavorings may be chosen from synthetic flavor oils and flavoring aromatics and/or oils, oleoresins and extracts derived from plants, leaves, flowers, fruits, and so forth, and combinations thereof. Non-limiting representative flavor oils include spearmint oil, cinnamon oil, oil of wintergreen (methyl salicylate), peppermint oil, Japanese mint oil, clove oil, bay oil, anise oil, eucalyptus oil, thyme oil, cedar leaf oil, oil of nutmeg, allspice, oil of sage, mace, oil of bitter almonds, cassia oil, and the like, and combinations thereof. Also useful flavorings include artificial, natural and synthetic fruit flavors such as citrus oils including lemon, orange, lime, grapefruit, yazu, sudachi, and fruit essences including apple, pear, peach, grape, blueberry, strawberry, raspberry, cherry, plum, pineapple, apricot, banana, melon, apricot, ume, cherry, raspberry, blackberry, tropical fruit, mango, mangosteen, pomegranate, papaya, watermelon, and the like, combinations thereof.

Other potential flavors which can be used include milk flavor, butter flavor, cheese flavor, cream flavor, and/or yogurt flavor; vanilla flavor; tea or coffee flavors, such as green tea flavor, oolong tea flavor, and the like; cocoa flavor, chocolate flavor; mint flavors, such as peppermint flavor, spearmint flavor, and Japanese mint flavor, and the like; spicy flavors, such as asafetida flavor, ajowan flavor, anise flavor, angelica flavor, fennel flavor, allspice flavor, cinnamon flavor, camomile flavor, mustard flavor, cardamom flavor, caraway flavor, cumin flavor, clove flavor, pepper flavor, coriander flavor, sassafras flavor, savory flavor, Zanthoxyli Fructus flavor, perilla flavor, juniper berry flavor, ginger flavor, star anise flavor, horseradish flavor, thyme flavor, tarragon flavor, dill flavor, capsicum flavor, nutmeg flavor, basil flavor, marjoram flavor, rosemary flavor, bayleaf flavor, and/or wasabi (Japanese horseradish) flavor, and the like; floral flavors; sour flavors, such as flavors formed from malic acid, citric acid, and/or ascorbic acid, and the like; and/or vegetable flavors. Commonly used flavors include mints such as peppermint, menthol, spearmint, berry mint, ginger mint, ginseng mint, green tea mint, artificial vanilla, cinnamon derivatives, and various fruit flavors, whether employed individually or in admixture. Flavors may also provide breath freshening properties, particularly the mint flavors. In some embodiments, flavors mimicking cocktails may be utilized such as cosmopolitan or mojito flavors.

Preservatives

Optionally, one or more preservatives may additionally be utilized herein. Preferred preservatives include, for example, sorbate, benzoate, and polyphosphate preservatives. Preferably, wherein a preservative is utilized herein, one or more sorbate or benzoate preservatives (or mixtures thereof) are utilized. Sorbate and benzoate preservatives suitable for use in the present invention include sorbic acid, benzoic acid, and salts thereof, including (but not limited to) calcium sorbate, sodium sorbate, potassium sorbate, calcium benzoate, sodium benzoate, potassium benzoate, and mixtures thereof.

Antioxidants

Antioxidants are molecules that inhibit oxidation of other molecules. Some antioxidants also function as preservatives. The present composition may include one or more antioxidants to provide health benefits or preservative effects to the composition. The composition may include any of the following antioxidants: ascorbyl palmitate, ascorbyl stearate, calcium ascorbate, dilauryl thiodipropionate, distearyl thiodipropionate, ascorbic acid, glutathione, lipoic acid, uric acid, glucose oxidase, potassium ascorbate, propyl gallate, sodium ascorbate, thiodipropionic acid, and tocophenol. The composition may also include any of the following antioxidants that may also serve as preservatives: calcium bisulfite, calcium hydrogen sulfite, isopropyl citrates, lactic acid, potassium bisulfite, sodium bisulfite, sodium sulfite, and sulfur dioxide.

Alertness Aids

In embodiments, the composition of the present disclosure may include active ingredients which aid in increased alertness and provide increased energy. In embodiments, the active ingredients may include caffeine extract, guarana, ginseng, ginko, yerba mate, green tea extract, taurine, kola nut extract, rhodiola root extract, minerals such as, for example, iodine, among others, vitamins such as for example vitamin B12, niacin, and vitamin D, among others, amino acids, and combinations thereof. In embodiments, the active ingredient may be caffeine extract. In some embodiments, caffeine is excluded from the compositions.

Alcohol

In an exemplary embodiment, the composition may be combined with alcohol to produce an alcoholic beverage. This may be desirable for individuals who wish to have a burst of energy and/or blood flow during social situations or other times that one would be ingesting alcohol. The composition may include various types of alcoholic beverages including liquor, beer, hard cider, wine, malt beverages, and liqueurs. Liquors include hard alcohols or distilled spirits such as rum, vodka, tequila, whiskey, and gin that have an alcohol (ethanol) content of about 30% to about 70%. Most liquors have an ethanol content of 40%. Beer includes drinks made of fermented starches and typically has an alcohol content of about 1% to about 20%, though typically beer has about 4% to 6% alcohol by volume. Hard cider is produced from fermented fruit and can have an alcohol content of about 1% to about 15%. Wine is produced from fermented grapes and may have an alcohol content of about 5% to about 20%, though most wines fall into the range of 12% to 15% alcohol by volume. Preferably, the alcoholic beverage composition contains about 10 to about 18 grams of alcohol (ethanol) per serving. More preferably the alcoholic beverage includes about 14 grams of alcohol per serving. For typical alcoholic beverages, this would be about 12 ounces of beer, 5 ounces of wine, or 1.5 ounces of liquor.

Herbs and Spices

In some embodiments, the composition may include one or more herbs and spices. Herbs are plants used for flavoring, food, medicine, or fragrances. In cuisine, herbs refer to the leafy green or flowering parts of a plant. Spices, similar to herbs, are plants used for flavoring, coloring, or preserving food. Spices are distinguished from herbs in that they are made from seeds, fruits, roots, barks or other parts of plants other than leaves and flowers. Herbs and spices that may be included in the present composition to provide particular flavors include, for example, allspice, anise, avocado leaf, basil, bay leaf, caper, caraway, cardamom, cayenne pepper, celery, chicory, chili pepper, chives, chuchuhuasi, cicely, cilantro, cinnamon, clove, coriander, cumin, curry, dill, elderflower, fennel, fingerroot, galangal, garlic chives, ginger, horseradish, jasmine, Jiaogulan, juniper, lavender, lemon balm, lemon verbena, lemongrass, licorice, maca, marjoram, mint, mustard, nutmeg, oregano, orris root, paprika, parsley, pepper, peppermint, quassia, *Rhodiola rosea* (golden root), rosemary, rue, safflower, saffron, sage, sassafras, savory, Schizandra berries, spearmint, star anise, sumac, Szechuan pepper, tarragon, thyme, turmeric, vanilla, wasabi, watercress, wattleseed, wintergreen, wormwood, and yarrow. Herbs may also be incorporated into exemplary compositions for medicinal or therapeutic purposes. Gingko biloba, ginseng, dandelion, ginger, and licorice may be included in compositions to increase alertness, immune function, and physical stamina.

Vitamins and Minerals

In some embodiments, the composition may include one or more vitamins and minerals. Vitamins are organic compounds that organisms must ingest because they cannot synthesize them in sufficient quantities. Vitamins that may be included in the present composition include retinol (Vitamin A), beta carotene (Vitamin A), thiamine (Vitamin $B_1$), riboflavin (Vitamin $B_2$), niacin (Vitamin $B_3$), pantothenic acid (Vitamin $B_5$), pyridoxine (Vitamin $B_6$), biotin (Vitamin $B_7$), folic acid (Vitamin $B_9$), cyanocobalamin (Vitamin $B_{12}$), ascorbic acid (Vitamin C), cholecalciferol (Vitamin D), ergocalciferol (Vitamin D), tocopherol (Vitamin E), and phylloquinone (Vitamin K). Minerals are essential nutrients other than common organic molecules. Minerals that may be included in the present composition include calcium, phosphorus, potassium, sodium, chlorine, magnesium, iron, cobalt, copper, zinc, manganese, molybdenum, iodine, and selenium.

Amino Acids and Fatty Acids

In some embodiments, the composition may include one or more additional amino acids and/or fatty acids. Amino acids other than arginine, citrulline, and taurine may be included in exemplary compositions. Essential amino acids are amino acids that cannot be synthesized by the organism. In the case of humans, essential amino acids include phenylalanine, valine, threonine, tryptophan, methionine, leucine, isoleucine, lysine, and histidine. Any of these essential amino acids may be included in the present compositions. Amino acids included in exemplary compositions may also be conditionally essential or dispensable to the human or animal's diet. Other such amino acids may include cysteine, glycine, glutamine, proline, tyrosine, alanine, aspartic acid, asparagine, glutamic acid, selenocysteine, pyrrolysine and serine.

Fatty acids may be included in exemplary compositions. Essential fatty acids are fatty acids that cannot be synthesized by the organism. In the case of humans, essential fatty acids include alpha-linoleic acid (an omega-3 fatty acid) and linoleic acid (an omega-6 fatty acid). Other fatty acids may be included that are non-essential fatty acids such as other omega-3 and omega-6 fatty acids including docosahexanoic acid and gamma-linolenic acid.

Lipids may be included in the compositions in the form of lipid emulsions that may include fatty acids, lecithin from egg yolks, glycerol, and water.

Food and Drink Ingredients

In some embodiments, the composition may include one or more food and drink ingredients such as juices, fruits, nuts, seeds, vegetables, chocolate, grains, oils, dairy, eggs, meats, seafood, and edible fungi. Exemplary juices that may be incorporated into beverage compositions may include wheatgrass juice, apple juice, coconut water, lemon juice, orange juice, pineapple juice, beet juice, carrot juice, cucumber juice, and tomato juice, among others. Fruits and vegetables may be included in non-liquid compositions and may preferably be dried. Dried fruit enjoys a longer shelf life, making it an appealing ingredient in solid food bars that are packaged for later consumption. Examples of dried fruits include raisins, dates, prunes, figs, apricots, pomegranates, acai, pineapples, cherries, blueberries, cranberries, peaches, apples, and pears, among others. Examples of vegetables include peas, carrots, spinach, cabbage, broccoli, kale, beets, and tomatoes, among others. Exemplary nuts may include hazelnuts, almonds, pecans, pistachios, walnuts, and cashews, among others. Exemplary seeds may include chia, flax, sesame, and sunflower seeds, among others. Exemplary grains include rye, wheat, quinoa, rice, corn, barley, and oats, among others.

Other Functional Ingredients

In embodiments, the confectionery nutritional supplements of the present disclosure may include active ingredients for male vitality, for enhancing muscle growth and/or which alleviate symptoms of erectile dysfunction or sexual dysfunction. The active ingredients may include didehydroepiandrosterone (DHEA), *Panax ginseng*, guarana extract, horny goat weed, *Eurycoma longifolia*, Tongkat Ali, *Xanthoparmelia Scabrosa, Cnidium Monieri, Mucuna Pruriens*, and/or other plant extracts within the purview of those skilled in the art, and combinations thereof.

Other functional ingredients may include binders, emulsifiers, soluble fibers, stabilizers, anticaking agents, enzymes, and thickening agents. One exemplary emulsifier is lechithin.

Additional nutritional ingredients may include CoQ10, lutein, phytonutrients, lycopene, mycoprotein, cordyceps, ornithine, melatonin, and frankincense.

Compositions

Various compositions are possible which include the novel combination of arginine, citrulline, and taurine. Such compositions may exist as liquid concentrates, solid concentrates, liquid beverages, solid food items, and other ingestible compositions. Exemplary formulas for various types of compositions are provided below in Tables 1-8.

In an embodiment, the nutritional compositions are administered to the individual so as to provide the individual a liquid, such as a beverage. The term "beverage composition" as used herein denotes a composition that is single-strength and ready to drink, that is, drinkable. As used herein, "beverage concentrate" refers to a concentrate that is either in concentrated liquid form or in essentially dry mixture form, and which need to be reconstituted by addition of a liquid such as water. The term "non-liquid food composition" refers to a solid food product that is ready to eat and includes the amino acids of the present disclosure.

The nutritional compositions of the present disclosure may be provided to an individual or patient in one bolus, or several smaller doses. In some instances, the individual may wish to treat an endothelial dysfunction with regular treatments over a long period of time. In such instances, the individual may take the composition on a regular schedule. For example, the individual may take a dose once a day, twice a day, three times a day, four times a day, five times a day, and the like. Alternatively, an individual may simply wish for a quick boost in vasodilation in preparation for physical activity or to recover from fatigue. In such instances, the individual may take one dose either immediately following experiencing fatigue or some period of time before engaging in physical activity. For example, the period of time may be 4 hours, 2 hours, 1 hour, 30 minutes, 10 minutes, or 5 minutes.

Additional ingredients, as described above, may be included in the compositions to provide particular flavors, nutritional benefits, or functional benefits. For example, to aid in recovering from fatigue, the composition may include caffeine. In another example, to prepare the individual for physical activity, the composition may include carbohydrates to fuel the individual.

In one embodiment, the composition is provided as a concentrated, solid dry composition. Alternatively, the beverage concentrate may be provided as a cube, a quickly disintegrating tablet, or effervescent tablets, beads, and powders. The composition may be, for example, in powder, granule, or tablet form. In the exemplary formula of Table 1, the composition is provided as a dry composition that can be encapsulated or pressed into tablets with appropriate excipients. Encapsulation is preferred because the amino acids (particularly arginine) can have an unappealing ammonia taste and the capsules hide the flavor.

TABLE 1

Pill composition

| Component | Conc. (Wt-%) | Conc. (Wt-%) | Conc. (Wt-%) |
|---|---|---|---|
| Arginine | 30-60 | 35-50 | 40-45 |
| Citrulline | 20-50 | 25-40 | 30-35 |
| Taurine | 10-40 | 15-30 | 20-25 |

Dry solid compositions may also include additional ingredients to form a dry powder beverage concentrate. Such compositions are intended to be diluted with water or other diluents to produce a beverage. The compositions may be packaged in individual servings or may be measured from a large container of powder. An exemplary formula for a dry beverage concentrate is provided in Table 2. Such concentrates preferably include sweetener to mask the taste of amino acids and other functional ingredients to produce a beverage.

TABLE 2

Beverage concentrate (dry powder)

| Component | Conc. (Wt-%) | Conc. (Wt-%) | Conc. (Wt-%) |
|---|---|---|---|
| Arginine | 6.5-19 | 9.5-16 | 10.5-15 |
| Citrulline | 5-16 | 7.5-13 | 8.5-12 |
| Taurine | 3-11 | 5.2-8.8 | 6-8 |
| Sweetener | 30-75 | 41-63 | 49-54.5 |
| Other functional ingredients | 1-30 | 7-25 | 15-21 |

The nutritional composition may come in the form of a liquid concentrate instead of a solid concentrate. Exemplary formulas for a liquid concentrate may include the amino acids, sweetener, water, and other functional ingredients. Table 3 illustrates possible quantities of each of those components. The concentrate may be ingested quickly in a "shot" much like 5-hour ENERGY®. Alternatively, the concentrate may be mixed with additional water or other liquid to produce a beverage.

TABLE 3

Beverage concentrate (liquid)

| Component | Conc. (Wt-%) | Conc. (Wt-%) | Conc. (Wt-%) |
|---|---|---|---|
| Arginine | 2.5-6.5 | 3.6-5.4 | 4.1-4.9 |
| Citrulline | 2-5 | 2.7-4.2 | 3.2-3.8 |
| Taurine | 1-3.5 | 1.8-2.7 | 2.1-2.4 |
| Sweetener | 10-25 | 14-22 | 16.5-19.5 |
| Other Functional Ingredients | 3-10 | 5-8 | 5.8-7 |
| Water | 50-81.5 | 57.7-72.9 | 62.4-68.3 |

Exemplary alcoholic beverage compositions may include cocktails, wine spritzers, shots or shooters, and the like. Table 4 below shows exemplary formulas for such alcoholic beverage compositions. Depending on the form, the composition may include varying quantities of alcoholic beverage due to differing alcohol content. An exemplary shot may include from about 70 wt-% to about 95 wt-% liquor in addition to arginine, citrulline, and taurine. Such a shot may include approximately 1.5 ounces of rum, vodka, tequila, or other distilled spirits. Shots may further include sweeteners, flavorings, and other functional ingredients. Wine spritzers may include from about 35 wt-% to about 60 wt-% wine in addition to arginine, citrulline, taurine, and carbonated water. The spritzer may include about 4 to about 5 ounces of wine and about 3 to about 5 ounces of carbonated water. The wine spritzer could include additional ingredients such as sweeteners and other flavorings such as fruit juices. A variety of alcoholic cocktails including arginine, citrulline, and taurine are possible. Typically, cocktails will include about 1 wt-% to about 30 wt-% liquor, or about 1.5 ounces of liquor. Various combinations and amounts of other liquids, sweeteners, and flavoring are possible.

An alcoholic beverage composition may be pre-packaged in ready-to-drink form. In other embodiments, a portion of the beverage composition, including the amino acids, is pre-packaged and is intended to be mixed with additional ingredients to create an alcoholic beverage. For example, the pre-packaged product could include arginine, citrulline, taurine, sweetener, flavorings, and liquor. This product could be ingested alone as a shot, or combined with water, carbonated water, or other liquids to produce a cocktail. In some embodiments, alcoholic beverage compositions are preferably free or substantially free of caffeine.

TABLE 4

Alcoholic beverage

| Component | Conc. (Wt-%) | Conc. (Wt-%) | Conc. (Wt-%) |
| --- | --- | --- | --- |
| Arginine | 1-15 | 1.2-10 | 1.5-7.5 |
| Citrulline | 0.9-12 | 1-8 | 1.1-5.5 |
| Taurine | 0.5-9 | 0.6-6 | 0.7-4 |
| Alcoholic beverage | 5-95 | 10-85 | 15-75 |
| Sweetener | 0-50 | 2-35 | 5-25 |
| Other Functional Ingredients | 0-40 | 0.1-25 | 1-10 |
| Water | 0-90 | 10-80 | 20-70 |

In another exemplary embodiment, arginine, citrulline, and taurine may be provided in a ready-to-drink enhanced water beverage. Such exemplary beverages include but are not limited to, sodas, energy drinks, juices, elixirs, rehydration beverages, pre- and post-work out sports beverages, isotonic beverages, hypertonic beverages, hypotonic beverages, dietary supplemental drinks and enhanced beverages. Table 5 includes exemplary formulations for such beverages which may include sweeteners, water, and other functional ingredients. The water may be carbonated. Various caloric or non-caloric sweeteners may be included. The various functional ingredients discussed above may be included as well. In one exemplary embodiments, a ready-to-drink beverage may include artificial flavoring, sugar, and treated water. Such a beverage may be ingested after a flight to remedy jetlag or after a workout to replenish energy and fluids.

TABLE 5

Enhanced water beverage

| Component | Conc. (Wt-%) | Conc. (Wt-%) | Conc. (Wt-%) |
| --- | --- | --- | --- |
| Arginine | 0.75-2.25 | 1-2 | 1.3-1.7 |
| Citrulline | 0.57-1.73 | 0.8-1.5 | 1.0-1.3 |
| Taurine | 0.38-1.12 | 0.5-1 | 0.6-0.9 |
| Sweetener | 0-15 | 2-12 | 5-7 |
| Other Functional Ingredients | 0-25 | 1-5 | 1.8-2.4 |
| Water | 54.9-98.3 | 78.5-94.7 | 86.7-90.3 |

In other embodiments, the nutritional compositions are administered to the individual so as to provide the individual a non-liquid food product. Such exemplary non-liquids include but not limited to gelatins, chews, gels, capsules, pills, wafers, bars, sweets, cookies, biscuits, lozenges, gummy candies, chewing gum, and other confections. The non-liquid composition may be in the form of a variety of shapes including a pellet, a tablet, a capsule, a ball, a pillow, a chunk, a stick or a slab, among others.

In one exemplary embodiment, the non-liquid food composition may be a nutrition or protein bar that includes food ingredients in addition to arginine, citrulline, and taurine. The non-liquid food composition may include a protein source, a carbohydrate source, and one or more additional ingredients. Table 6 provides exemplary formulations of such compositions. In one exemplary embodiment, the non-liquid food composition is a nutrition bar including oats as a carbohydrate source, peas and peanut butter as a protein source, coconut, and chocolate. In another exemplary embodiment, the non-liquid food composition is a nutrition bar including egg white protein, honey as a carbohydrate source, citrus, and jalapeno. Various combinations of ingredients are possible.

In some embodiments, the nutrition or protein bar may include chocolate, maltitol, and sucrose in addition to arginine, citrulline, and taurine. The arginine, citrulline, and taurine may be combined with the chocolate, maltitol, and sucrose to create layers sandwiched between additional layers of chocolate. Additional configurations of bars are possible.

TABLE 6

Non-liquid food composition

| Component | Conc. (Wt-%) | Conc. (Wt-%) | Conc. (Wt-%) |
| --- | --- | --- | --- |
| Arginine | 4-30 | 6-18 | 8-12 |
| Citrulline | 3-25 | 4.5-12 | 6-9 |
| Taurine | 2-20 | 3-10 | 4-6 |
| Carbohydrate | 10-50 | 20-40 | 25-35 |
| Protein | 0-60 | 10-50 | 30-45 |
| Other Functional Ingredients | 1-30 | 5-15 | 8-12 |

In another exemplary embodiment, the non-liquid food composition may be in the form of gels, chews, gummies, or jelly candies. In addition to arginine, citrulline, and taurine, the gel chew compositions may include gelling agents, carbohydrates, and other additional ingredients. Gelling agents may include pectin and gelatin. Appropriate carbohydrates may include cane sugar, maltodextrin, and honey. Exemplary formulas are provided below in Table 7. Gels or chews may be effective ways to ingest smaller quantities of the amino acids at a time to produce sustained effects over a period of time. Alternatively, the gels or chews may be formulated to provide a burst of energy and/or blow flow in a short period of time, such as an hour or less.

TABLE 7

Gel chews

| Component | Conc. (Wt-%) | Conc. (Wt-%) | Conc. (Wt-%) |
| --- | --- | --- | --- |
| Arginine | 1-15 | 4-12 | 7-9 |
| Citrulline | 1-11 | 3-9 | 5-7 |
| Taurine | 1-7 | 2-6 | 3-5 |
| Gelling Agent | 10-30 | 15-25 | 18-22 |
| Carbohydrate | 30-90 | 40-80 | 50-70 |
| Functional Ingredients | 0.1-10 | 0.5-5 | 1-3 |
| Water | 0.001-20 | 0.1-10 | 1-5 |

In another embodiment, the nutritional composition may be produced in a concentrated form to be later diluted by an individual at the time of consumption. The concentrated form of the nutritional composition may be in a powder, an effervescent tablet, a syrup, or a concentrated liquid. In a powder, the arginine, citrulline, and taurine may be combined with flavorings, sweeteners, and preservatives. The powder formulation may include citric acid as a flavoring and preservative. Silicon dioxide may be included as a flow agent.

In yet another embodiment, the nutritional composition may be formulated for use as a total parenteral nutrition (TPN) solution or an enteral tube nutrition solution (ETN). Such solutions are administered to individuals through cathethers or intravenous methods (TPN) or a feeding tube (ETN). Such methods of providing nutrition to an individual are often utilized when the body is placed into a state of torpor, or deep sleep. Humans may be placed in medical torpor while the body is under duress or trauma. In some instances, humans or other mammals may be induced into torpor to hibernate during space travel. Missions to more distant locations in space take a very long time and staying fully awake for the whole trip is not always the best option. Nutritional compositions including arginine, citrulline, and taurine help the body to heal or adjust to travel conditions by improving endothelial health. Improved endothelial health leads to improved blood flow and oxygen transport. An example of a TPN solution is provided in Table 8.

TABLE 8

Total parenteral nutrition

| Component | Conc. (Wt-%) | Conc. (Wt-%) | Conc. (Wt-%) |
| --- | --- | --- | --- |
| Arginine | 0.1-0.8 | 0.29-0.52 | 0.389-0.431 |
| Citrulline | 0.1-0.65 | 0.29-0.44 | 0.389-0.388 |
| Taurine | 0.1-0.50 | 0.20-0.35 | 0.292-0.302 |
| Carbohydrate | 5-17 | 8-15.5 | 10.9-14.0 |
| Other Amino Acids | 0.8-5.0 | 2.0-3.8 | 3.21-3.23 |
| Electrolytes | 21-50 | 26.5-41.5 | 34.0-34.4 |
| Lipids | 0.9-5 | 1.22-4.37 | 1.70-3.45 |
| Vitamins/Minerals | 0.2-1.2 | 0.29-0.87 | 0.39-0.65 |
| Water | 20-70 | 32-61 | 43-49 |

Methods of Making

Also provided herein are methods of making nutritional compositions. The nutritional compositions may be pills, powder concentrates, liquid concentrates, alcoholic beverages, ready to drink beverages, non-liquid food compositions, and gel chew compositions.

To make a pill containing arginine, citrulline, and taurine, the amino acids are combined together. The amino acids may be encapsulated or pressed into tablets with appropriate excipients.

Dry beverage concentrate compositions are made by combining arginine, citrulline, taurine, sweetener, and other functional ingredients into a consistent powder composition. The dry beverage concentrate may be packaged into individual servings in envelopes or other packaging. Alternatively, the concentrate may be packaged in bulk containers to be measured out into individual servings by a user. These dry ingredients may be diluted with water, juice, flavored soda, liquor, wine, wine cooler, malt beverage, malt liquor, or cider to produce a beverage for human consumption.

A liquid beverage composition is made by combining arginine, citrulline, taurine, sweetener, and other functional ingredients. These ingredients are then blended with water or other ingestible liquids to produce a beverage concentrate. The beverage concentrate is packaged into bottles or other containers. The beverage concentrate may be ingested as a quick "shot" to rapidly administer the amino acids. Alternatively, the beverage concentrate may be diluted with water, juice, flavored soda, liquor, wine, wine cooler, malt beverage, malt liquor, or cider to produce a beverage.

A method of making a ready to drink beverage is provided. The beverage may or may not contain alcohol. Dry ingredients of arginine, citrulline, taurine, sweetener, and other functional ingredients are blended together. The dry ingredients are mixed into a diluent such as water, juice, soda, or an alcoholic beverage. The resulting beverage is packaged into a can, a bottle, a carton, or a box.

A method of making a non-liquid food product having arginine, citrulline, and taurine is provided. The dry ingredients of the non-liquid food product are combined with any liquid ingredients and formed into solid shapes.

Also provided herein are methods of making gel chews having arginine, citrulline, and taurine. The ingredients of the gel chews are combined and shaped into chews.

Also provided herein are methods of making TPN solutions having arginine, citrulline, and taurine. The ingredients of the TPN solutions are combined and stored in bags.

Methods of Treatment

Provided herein are methods of improving endothelial health in a human or an animal by administering a composition comprising arginine, citrulline, and taurine. The composition may be diluted with water to produce a beverage. The beverage may also contain a sweetener and one or more functional ingredients. Alternatively, the composition may be administered as a tablet or in a capsule.

In other embodiments, methods of treating endothelial dysfunction is provided. Endothelial dysfunction may contribute to various conditions including hypertension, type I and II diabetes, hypercholesterolanemia, and coronary artery disease. An individual is treated by administering a composition comprising arginine, citrulline, and taurine.

Additionally, increased vasodilation has benefits for individuals that are healthy in that blood flow is increased. Increased blood flow can improve performance in physical activity or help to reduce fatigue. Increased blood flow can assist with resistance to or recovery from altitude sickness, decompression sickness, or jet lag. A composition comprising arginine, citrulline, and taurine is administered to the individual. The composition may be administered before a flight to prevent the effects of jet lag. Alternatively the composition may be administered during a flight to alleviate oncoming effects of jet lag. In another alternative, the composition may be administered after a flight to alleviate the effects of jet lag. In other embodiments, the composition may be administered to an individual to prevent or alleviate fatigue in general. Within about 5 minutes to about 4 hours, the individual will experience increased energy and blood flow.

In some embodiments, methods of treating sexual dysfunction are provided. A composition comprising arginine, citrulline, and taurine is administered to the individual suffering from sexual dysfunction. Within about an hour, the individual will experience increased blood flow to the genitals.

In the context of the brain, increased NO production leads to increased vasodilation and blood flow to the brain, as well as other benefits. For example, NO serves as a signaling molecule involved in interactions between neurons. NO increases the robustness of synapses, improving long term potentiation (LTP). LTP is directly related to memory and brain function. NO also upregulates guanylate cyclase (GC), which catalyzes cyclic guanosine monophosphate (cGMP) synthesis. NO also upregulates cyclic nucleotide-gated channels, large conductance calcium-activated potassium channels, ryanodine receptor calcium release channels, and the ADP-ribosyltransferases, all of which are implicated in memory processing. In some embodiments, a composition comprising arginine, citrulline, and taurine is administered to an individual to enhance mental agility. The composition causes blood flood to increase to the brain, allowing for more efficient delivery of energy to the brain and more efficient removal of waste from the brain. Memory can be strengthened by administering these compositions.

In some aspects, methods of treating altitude sickness and decompression sickness are provided. High altitudes cause blood vessels to constrict, causing individuals who are not accustomed to high altitudes to become sick. This is a common problem for people traveling to mountainous areas for activities such as skiing or rock climbing. Administration of the compositions including arginine, citrulline, and taurine help to counteract the blood vessel constriction by promoting vasodilation. Returning to normal altitudes after diving to very low altitudes areas, in activities such as scuba diving, can result in decompression sickness or "the bends." Improved vasodilation resulting from the administration of compositions including arginine, citrulline, and taurine can help alleviate blockages caused by nitrogen bubbles in the bloodstream.

In some embodiments, methods of providing nutrition to individuals in a state of torpor are provided. Nutritional solutions can be administered intravenously or through feeding tubes. Compositions including arginine, citrulline, and taurine help to promote endothelial health while individuals are in a sleep state.

In another embodiment, methods of improving endothelial health in animals are provided. A composition comprising arginine, citrulline, and taurine is administered to the animal. The composition may be combined with animal feed or diluted in water for easy consumption by the animal.

EXAMPLES

Example 1

Figure 1B:
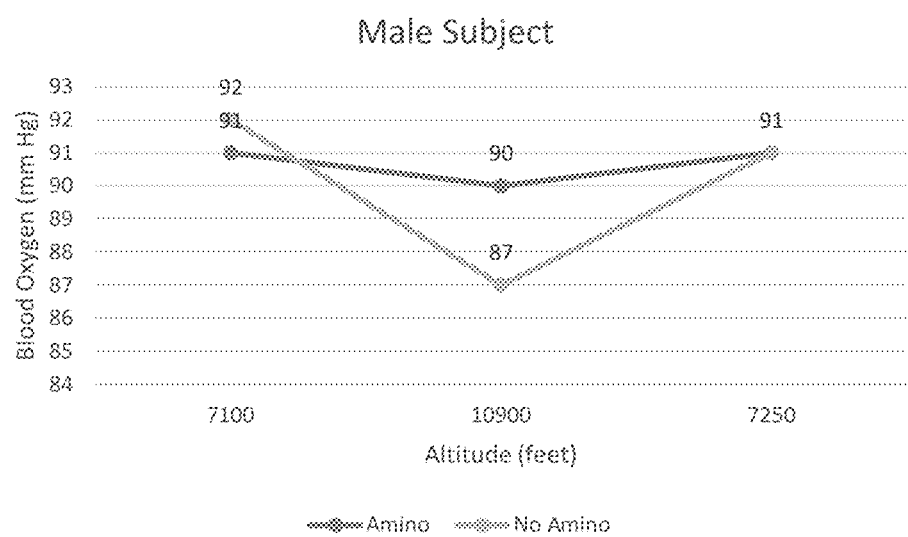
FIG. 1B depicts a graph comparing blood oxygen levels for a male subject having consumed or not consumed the claimed composition at various altitudes.

Blood oxygen levels were measured at various altitudes with the variable being consumption of an amino acid blend including arginine, citrulline, and taurine. Various mountain passes were used to provide an environment of going from a lower altitude (<8000 ft) to high altitude (>8500 ft). Blood oxygen levels were measured using a finger tip Acc U Rate brand oximeter. Altitude readings were taken by Apple I-Phone 7. The results while limited in scope indicate that blood oxygen levels remain at a higher level when the amino acid blend is consumed versus if no amino acids are consumed. Data for a female subject is summarized in FIG. 1A and data for a male subject is summarized in FIG. 1B.

While certain embodiments have been described, other embodiments may exist. While the specification includes a detailed description, the invention's scope is indicated by the following claims. The phrase "consisting essentially of" limits the scope of the claim to the specified materials including only minor impurities or inactive agents that a person of ordinary skill in the art would ordinarily associate with the listed components. The specific features and acts described above are disclosed as illustrative aspects and embodiments of the invention. Various other aspects, embodiments, modifications, and equivalents thereof which, after reading the description herein, may suggest themselves to one of ordinary skill in the art without departing from the spirit of the present invention or the scope of the claimed subject matter.

What is claimed is:

1. A method of making a beverage for increasing vasodilation, the method comprising:
    blending together the following dry ingredients:
        from about 5 wt. % to about 25 wt. % arginine,
        from about 3 wt. % to about 20 wt. % citrulline,
        from about 1 wt. % to about 15 wt. % taurine,
        from about 40 wt. % to about 75 wt. % sweetener, and
        from about 0.1 wt. % to about 10 wt. % other functional ingredients; and
    diluting the dry ingredients with one or more liquid ingredients selected from water, carbonated water, juice, flavored soda, liquor, wine, wine cooler, malt beverage, malt liquor, and cider;
    wherein the one or more liquid ingredients are present at a concentration of at least 40 wt. % of the total weight of the dry ingredients and the one or more liquid ingredients; and
    mixing to produce a beverage having at least 0.38 wt. % taurine.

2. The method of claim 1, wherein the dry ingredients are diluted with the one or more liquid ingredients at a concentration of at least 75 wt. % of the total weight of the dry ingredients and the one or more liquid ingredients.

3. The method of claim 1, wherein the dry ingredients are diluted with carbonated water at a concentration of at least 90 wt. % of the total weight of the dry ingredients and the carbonated water.

4. The method of claim 1, further comprising packaging the beverage in a can, bottle, carton, or box.

5. The method of claim 1, wherein the beverage is an alcoholic beverage comprising from about 10 grams to about 18 grams of ethanol.

6. The method of claim 1, wherein the beverage further comprises caffeine.

7. A method of making an enhanced water beverage, the method comprising:
    blending together the following dry ingredients:
        from about 5 wt. % to about 25 wt. % arginine,
        from about 3 wt. % to about 20 wt. % citrulline, and
        from about 1 wt. % to about 15 wt. % taurine;
    diluting the dry ingredients with one or more liquid ingredients selected from water, carbonated water, and flavored soda;
    wherein the one or more liquid ingredients are present at a concentration of at least 40 wt. % of the total weight of the dry ingredients and the one or more liquid ingredients; and
    mixing to produce an enhanced water beverage for increasing vasodilation, the enhanced water beverage having at least 0.38 wt. % taurine and at least 0.57 wt. % citrulline.

8. The method of claim 7, wherein the dry ingredients further comprise sucrose.

9. The method of claim 7, wherein the dry ingredients further comprise alertness aid.

10. The method of claim 7, wherein the dry ingredients further comprise ribose.

11. The method of claim 7, wherein the one or more liquid ingredients comprise carbonated water.

12. The method of claim 1, wherein the sweetener is selected from the group consisting of: sucrose, glucose, fructose, coconut palm sugar, date sugar, maple syrup, agave nectar, molasses, honey, brown rice syrup, cane juice, saccharin, sucralose, aspartame, acesulfame potassium, stevia, mogroside, erythritol, xylitol, sorbitol, maltitol, mannitol and mixtures thereof.

13. The method of claim 1, wherein the functional ingredients are selected from the group consisting of: flavoring agents, flavor enhancers, flavanols, acidulants, food acids, coloring agents, preservatives, antioxidants, alertness aids, alcohol, herbs, spices, extracts, vitamins, minerals, mineral salts, amino acids, fatty acids, juices, solid foods, and mixtures thereof.

14. The method of claim 1, wherein the functional ingredients comprise mineral salts selected from the group consisting of: potassium, sodium, and mixtures thereof.

15. The method of claim 1, wherein the functional ingredients comprise food acids selected from the group consisting of: malic acid, citric acid, tartaric acid, fumaric acid, lactic acid, adipic acid, calcium fumarate, phosphoric acid, succinic acid, and mixtures thereof.

16. A method of making a beverage for increasing vasodilation, the method comprising:
  blending together dry ingredients:
    L arginine;
    L citrulline;
    taurine;
    sweetener; and
    other functional ingredients; and
  mixing the dry ingredients with water to produce the beverage comprising:
    0.75 to 2.25 wt. % L-arginine;
    0.57 to 1.73 wt. % L-citrulline;
    0.38 to 1.12 wt. % taurine;
    up to 15.0 wt. % sweetener;
    up to 25 wt. % other functional ingredients; and
    54.9 to 98.3 wt. % water.

17. The method of claim 16, wherein the sweetener comprises at least 0.1 wt. % of ribose.

18. The method of claim 17, wherein the sweetener further comprises at least 0.1 wt. % of sucrose.

19. The method of claim 18, wherein the other functional ingredients comprise at least 0.1 wt. % of caffeine.

20. The method of claim 17, wherein the other functional ingredients comprise at least 0.1 wt. % of one or more B vitamins.

21. The method of claim 16, wherein the other functional ingredients comprise at least 0.1 wt. % of alertness aids.

22. The method of claim 16, wherein the other functional ingredients comprise at least 0.1 wt. % of citric acid.

23. The method of claim 16, wherein the beverage comprises at least 0.8 wt. % of L-citrulline.

24. The method of claim 16, wherein the beverage comprises at least 0.5 wt. % taurine.

* * * * *